United States Patent
Beck et al.

(10) Patent No.: US 6,852,094 B2
(45) Date of Patent: Feb. 8, 2005

(54) INFUSION SET ADAPTOR

(75) Inventors: Kent F. Beck, Layton, UT (US); James A. Malmstrom, Kaysville, UT (US); Scott D. Miles, Sandy, UT (US)

(73) Assignee: ZEVEX, Inc., Salt Lake City, UT (US)

( * ) Notice: Subject to any disclaimer, the term of this patent is extended or adjusted under 35 U.S.C. 154(b) by 0 days.

(21) Appl. No.: 10/606,262

(22) Filed: Jun. 25, 2003

(65) Prior Publication Data

US 2004/0097885 A1 May 20, 2004

Related U.S. Application Data

(63) Continuation of application No. 09/836,851, filed on Apr. 16, 2001, now Pat. No. 6,659,976.

(51) Int. Cl.[7] .............................................. A61M 5/30
(52) U.S. Cl. ........................ 604/67; 604/118; 604/246
(58) Field of Search ................... 251/4, 5, 6; 604/449, 604/65, 30, 31, 34, 66, 67, 118, 119, 246

(56) References Cited

U.S. PATENT DOCUMENTS

| | | | | |
|---|---|---|---|---|
| 5,672,887 A | * | 9/1997 | Shaw et al. ................. 250/573 |
| 5,720,721 A | * | 2/1998 | Dumas et al. ................. 604/67 |
| 5,810,323 A | * | 9/1998 | Winterer et al. ............... 251/4 |
| 5,826,621 A | | 10/1998 | Jemmott | |
| 6,110,153 A | * | 8/2000 | Davis et al. ................. 604/245 |
| 6,494,864 B1 | * | 12/2002 | Kerwin et al. ............... 604/131 |
| 6,659,976 B2 | * | 12/2003 | Beck et al. .................... 604/67 |

* cited by examiner

*Primary Examiner*—Edward K. Look
*Assistant Examiner*—John K. Fristoe, Jr.
(74) *Attorney, Agent, or Firm*—Bateman IP Law Group (57) ABSTRACT

A feeding set adaptor and related system for delivering solutions utilize a feeding set adaptor which engages a pump engaging portion of an infusion set and the feeding set adaptor structure to provide monitoring portions for detecting pressures within the infusion set, a sample cell for determining the presence of air within an infusion set, and an anti-freeflow device for selectively preventing freeflow through the infusion set. The feeding set adaptor is configured for mounting on an infusion pump which moves solution through the infusion set for delivery to a patient.

80 Claims, 7 Drawing Sheets

INFUSION SET ADAPTOR

RELATED APPLICATIONS

The present application is a continuation application of U.S. patent application Ser. No. 09/836,851 filed Apr. 16, 2001, now U.S. Pat. No. 6,659,976.

BACKGROUND OF THE INVENTION

1. Field of the Invention

The present invention relates to systems for feeding solutions to patients. More particularly, the present invention relates to a feeding set adaptor which is used in association with a medical solution pump. The pump and an infusion set which is acted on by the pump typically form a system for the monitoring of fluid pressures, for bubble detection and for selective flow occlusion of solutions being fed to a patient. Specifically, the invention relates to an adaptor which is used to connect various parts of an infusion set and to integrate them with the pump to enable the monitoring of fluid pressures, the detection of bubbles, and the selective occlusion of fluid flow to prevent freeflow conditions.

2. State of the Art

There are numerous situations in which a solution must be fed to a patient over a period of time. In some situations, the solution is provided directly into the blood stream of the patient. Saline solutions and medications supplied in such a manner are typically referred to as parenteral solutions.

In contrast to a parenteral system, an enteral feeding system is used to provide nutrient solutions to patients who, for one reason or another, are unable to eat for themselves. Such a system typically includes a pump which is attached to an input tube connected to a supply container and to an output tube which is connected to a patient. The pump draws nutrient solution from the supply container and delivers the solution to the patient. By adjusting the number of rotations of the motor, or the frequency of rotations, in the pump, an enteral feeding pump can adjust its output to deliver a predetermined amount of nutrient solution (or even medication) at a desired rate.

A significant problem with many currently available enteral feeding systems, is that the intake and output tubes may become occluded. Unlike parenteral solutions, enteral feeding solutions have a relatively high viscosity, as they must carry sufficient nutrition to sustain the patient. Occlusion can occur, for example, if a fibrous substance is included in the enteral feeding solution and somehow combines to interfere with flow through the tube. Occlusion can also occur if a tube is bent sufficiently to interfere with flow therethrough, or if a roller clamp (as is commonly used for intravenous applications) is not sufficiently opened. Because of the viscosity of the solution, the amount of kinking of the tube or other interference required to interfere with solution flow is significantly less than that required in a parenteral infusion set.

If the intake tube becomes occluded, insufficient solution may be supplied to the pump, and thus to the patient. If the output tube becomes occluded, the flow of, solution may be blocked, or the solution may be delivered suddenly at unusually high pressures. Additionally, medical personnel may fail to notice that the supply container is out of solution, or may not properly mount the intake and/or output tubes in the pump, thereby preventing the proper amount of solution from being delivered to the patient. Any of these scenarios can have tragic consequences if allowed to continue for a prolonged period of time.

Yet another concern with enteral feeding systems is that of viscosity of the solution and viscosity changes as a container full of solution is pumped to a patient. Knowing the viscosity of the fluid being pumped through the enteral feeding system is important because different viscosities are pumped at different rates by the enteral feeding pump. For example, a lower quantity of a highly viscous solution will be pumped by a given number of rotations of the enteral feeding pump motor than will be moved by the same pump when the solution has low viscosity. In other words, the amount of solution fed to the patient can differ substantially depending on the solution's viscosity. Thus, unless the pump is able to accurately determine and compensate for viscosity changes in the solution (i.e. by increasing or decreasing the rotations of the pump-rotor in a given period of time), it is difficult to know exactly how much of the solution has been fed to the patient.

Yet another problem which is of concern during the administration of enteral feeding solutions is the presence of air bubbles. While very small air bubbles will not cause harm, large bubbles entering the blood stream can cause serious medical complications and even death. Thus, it is important to monitor the solution to ensure that any bubbles present do not exceed the desired threshold.

Still another problem which is present in enteral feeding systems, and the like, is freeflow. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump, is placed along the infusion set to control the rate at which the solution is fed to the patient. In applications where a pump, etc., is used, the clamps used to regulate flow are typically opened to their fullest extent to prevent the clamp from interfering with the proper functioning of the pump. The clamp is opened with the expectation that the enteral feeding pump will control fluid flow through the infusion set.

It is not uncommon, for emergencies or other distractions to prevent the medical personnel from properly loading the infusion set in the enteral feeding pump. When the infusion set is not properly loaded in the pump and the clamp has been opened, a situation known as freeflow often develops. The force of gravity causes the solution to flow freely into the patient unchecked by the pump or other regulating device. Under a freeflow condition, an amount of solution many times the desired dose can be supplied to the patient within a relatively short time period. This can be particularly dangerous if the solution contains potent medicines and/or the patient's body is not physically strong enough to adjust to the large inflow of solution.

Numerous devices have been developed in an attempt to prevent free flow conditions. Such devices, however, typically add significantly to the overall cost of the infusion set and some provide only marginal protection against free flow. Thus, there is a need for, a device that prevents a freeflow condition while allowing controlled flow through the infusion set. There is also a need for such a device which prevents freeflow if an infusion set is not properly mounted in a pump or other regulating means. Furthermore, there is a need for a device which prevents freeflow and which is inexpensive and easy to use.

The fluid flow monitoring mechanism disclosed in U.S. Pat. No. 5,720,721 and the anti-freeflow mechanism described in U.S. Pat. No. 5,704,584 (both of which are expressly incorporated herein) provided a significant improvement in monitoring for enteral feeding pumps and in control of freeflow situations.

Figure 1A:
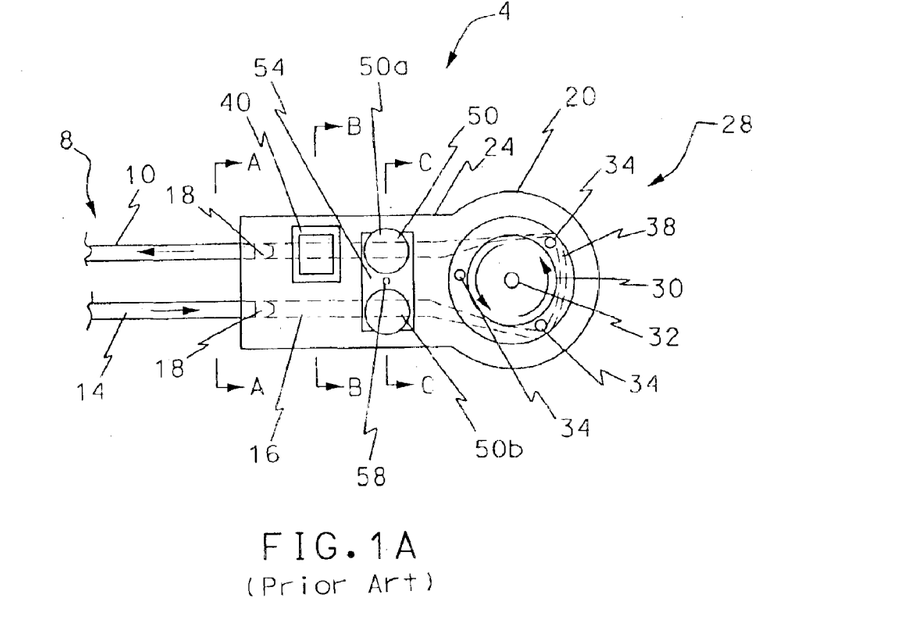
FIG. 1A shows a top view of an enteral feeding pump housing formed in accordance with the principles of the prior art.

As shown in FIG. 1A, the pump taught in U.S. Pat. No. 5,720,721 uses two pressure sensors to monitor viscosity and occlusions, and to enable the enteral feeding pump to compensate for the varying amount of solution which will pass through the pump with each rotation of the rotor. The pressure sensors engage the elastic tube of the infusion set and monitor changes in the strain on the infusion set by occlusions and viscosity changes. The strain information can then be processed by the pump and adjustments made to the number of rotations of the pump rotor to compensate. In the event that the occlusion is too severe to compensate by modification of the rotor rotations, the pump is shut down and an alarm signal generated so that replacement tubing may be provided.

Also included was an air detector which was disposed in the pump. The air detector was disposed in communication with the pump and used ultrasonic energy to determine if bubbles were present in the conduit.

While the pressure sensor system of U.S. Pat. No. 5,720,721 is a significant improvement over the art, it does have limitations. The pressure sensors described in the '721 patent are relatively expensive and must be properly mounted in the pump. Additionally, the person loading the pump must make sure that the upstream and downstream portions of the infusion set are properly loaded in the pump housing so that they engage the pressure sensors in the proper manner. Failure to properly load the infusion set can interfere with the functioning of the pressure sensors. In particular, if the clinician overly stretches the tubing as he or she wraps it around the pump, the tube on one side of the pump rotor will be stretched to a greater degree than the opposing side. This, in turn, can effect pump accuracy if too severe.

One manner for decreasing the costs of pressure sensors is to use an optical sensors. While there are several methods for using optical sensors to determine the presence of occlusions, each has significant drawbacks. Some methods only allow the mechanism to determine when the pressure exceeds a certain threshold. This is done by detecting when the expanding tube of the infusion set engages a surface, thereby modifying reflection or refraction of light. Other methods require complex calculations of refraction indexes or otherwise provide relatively limited information on small pressure changes. Additionally, some methods can vary based on the material from which the infusion set is formed, or based on whether the tube of the infusion set is opaque or transparent.

In addition to the above, many mechanisms for monitoring pressure within an infusion set lack an inherent failure detector. For example, if a sensor is configured to sense only when the expanding infusion set tube engages a transparent surface, the failure to record a reflected signal may mean that the tube has not expanded. In certain situations, however, the lack of reflected signal could also mean that the sensor has failed and is either not sending the signal or is not receiving the reflected signal.

In addition to the concerns with pressure sensing technology of the prior pumps, the pumps also used ultrasonic technology for bubble detection. While this technology is highly accurate, it is also expensive. An ultrasonic sensor can cost as much as 50 times as much as an optical sensor.

In addition to the above, the anti-freeflow technology discussed in U.S. Pat. No. 5,704,584 has limitations. While the occluder mechanism works well, it is relatively expensive to form a separate mechanism to selectively stop flow through the infusion set. A separate pinch clip occludes such as that shown in FIG. 1B can add fifteen to twenty percent to the cost of an infusion set. While the cost per unit is rather small, daily replacement of the infusion set can add up to significant costs. In a highly competitive medical environment, even a few cents per unit can dramatically effect sales quantities.

Thus, there is a need for a mechanism which can enable improved pressure monitoring, improved air detection and improved flow occlusion. Such a mechanism should be relatively inexpensive and should lessen the likelihood of errors in use of the pump and infusion set. Furthermore, it should enable the use of infusion sets made from a variety of materials.

SUMMARY OF THE INVENTION

Thus, it is an object of the present invention to provide a mechanism which allows improved method monitoring viscosity and/or occlusions in an infusion set.

It is another object of the present invention to provide such a mechanism which facilitates the monitoring of viscosity and occlusions with an optical sensor system.

It is another object of the present invention to provide a mechanism which facilitates the optical monitoring of solution to determine the presence of bubbles in the solution.

It is another object of the present invention to provide a mechanism which prevents free flow through an infusion set unless fluid flow through the infusion set is being driven by the pump.

It is yet another object of, the present invention to provide an integrated adaptor which is disposed along an infusion set which facilitates pressure monitoring, bubble monitoring and an anti-free flow device.

The above and other objects of the present invention are realized in specific illustrated embodiments of a feeding set adaptor configured for attachment to an upstream portion, a down stream portion and a pump engaging portion of an infusion set.

In accordance with one aspect of the invention, the feeding set adaptor is attached to a flexible tube which forms the pump engaging portion of the infusion set. The flexible tube is mounted to the adaptor in such a manner that the tube is not disproportionately stretched on either side of the pump mechanism when it is loaded on the pump mechanism.

In accordance with another aspect of the invention, the flexible tube of the infusion set attached to the feeding set adaptor has at least one monitoring portion which is held by the adaptor to prevent stretching of the tube. The monitoring portion is disposed adjacent a sensor which allows the pump to monitor pressure within the tube. Preferably, this is done by an optical sensor which is positioned to monitor the diameter of the tube. By sensing, changes in the diameter of the tube, the pump can determine the pressure within the tube. If the pressure sensed is above or below predetermined thresholds, the pump can determine that there is an occlusion and will generate an alarm.

In a preferred embodiment, the flexible tube is secured for monitoring both upstream and-downstream from the pump rotor (or other pump mechanism). Thus, the pump can monitor upstream and downstream occlusions. The pressure monitoring can also be used in conjunction with movement of the pump mechanism to more accurately determine solution flow through the pump system.

In a preferred embodiment, the feeding set adaptor is configured to hold the tube in such a position that the tube, neither obstructs all light flow nor allows complete light flow between the two sides of the optical sensor. Between the two extremes of receiving a full optical signal and no optical signal, the signals generated by the optical signal-receiver indicate the extent to which the optical signal sent by the optical signal emitter have been obstructed by the tube. If, however, a full reading is received, the pump can indicate that the feeding set adaptor and the associated tube have not been properly mounted in the pump. In contrast, if no reading is received, the pump can generate an alarm indicating that the sensor is malfunctioning, or that the infusion set tube has expanded well beyond the desired threshold.

In accordance with another aspect of the invention, the feeding set adaptor includes a sample cell through which solution being pumped by the pump is passed. The sample cell is configured for monitoring the solution to determine the presence of bubbles. Preferably, the sample cell has a pair of angled sidewalls. The angled sidewalls are preferably disposed at an angle of 47 to 70 degrees from each other, depending on the indices of refraction of the material used, and are most preferably angled 50 to 60 degrees from one another.

The sample cell is configured to fit into a void on a housing-disposed adjacent to an optical sensor. Light from the optical sensor passes through the housing and the sample cell in such a manner that it is refracted in one direction if the sample cell is full of liquid and another angle if a bubble is present in the sample cell. Thus, the pump is able to monitor for bubbles and to make appropriate corrections in pump flow rate or to generate an alarm if the amount of air present in the solution exceeds desired thresholds.

In accordance with one aspect of the invention, an occluder is disposed within the infusion set. The occluder is configured to prevent free flow of fluids in the infusion set past the occluder. The occluder is also configured, however, to selectively allow solutions to pass by the occluder which are pumped by an enteral feeding pump and the like.

In accordance with another aspect of the invention, the feeding set adaptor includes an occluder which prevents fluid flow through the infusion set when the infusion set has not been disposed in proper engagement with the pump mechanism of the infusion pump, thereby giving control of fluid flow through the infusion set to the pump.

In one embodiment of the invention, the occluder is formed by a stop attached to the feeding set adaptor and placed in the tubing of the infusion set. The stop limits flow through the tube by limiting flow around and/or through the stop when the solution is subject to flow due to gravity. However, when greater pressures are placed on the solution, such as those produced by a pump, the solution is able to flow around and/or through the stop, thereby delivering the solution to the patient.

In accordance with another embodiment of the present invention, an occluding valve is formed as part of the feeding set adaptor and is disposed in the infusion set. The valve prevents free flow through the infusion set due to gravity, while allowing controlled flow of solution through the infusion set.

In accordance with another aspect of the invention, the occluder is configured to stop fluid flow until the infusion set has been properly loaded into a control mechanism such as a pump. Once properly placed, the interaction between the occluder and the infusion set effectively opens the infusion set to allow solution to flow therethrough.

In accordance with still yet another aspect of the invention, a plurality of the aspects discussed above are integrated into a single feeding set adaptor. By integrating the various aspect discussed above, the health care professional or patient who loads the pump with the infusion set can be assured that the safety and monitoring aspects discussed above are being accomplished without the need to check multiple systems.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Referring to FIG. 1A, there is shown a top view of an enteral feeding system taught in U.S. Pat. No. 5,720,721. The enteral feeding system, generally indicated at 4, has a delivery set 8 including an intake (upstream) tube 10 and an output (downstream) tube 14 connected together by a pair of connectors 18 and a pump tubing segment within an enteral feeding pump 20. The position of the pump tubing segment disposed inside of the pump 20 is represented by the dashed lines 16.

The enteral feeding-pump 20 includes a housing 24 with a conventional motor unit, generally indicated at 28. The motor unit 28 includes a rotor 30 with a plurality of peristaltic rollers 34 disposed about an exterior of the rotor to move liquid through the enteral feeding pump 20. The rotor 30 is connected by a shaft 32 to a motor (not shown). The section 38 of the pump tubing segment 16 is disposed about the rotor 30 and rollers 34 and is usually made of a flexible silicone material. Rotating the rotor 30 in the direction indicated by the arrows directionally squeezes the tube section 38 and causes solution to be pushed through the output tube 14.

Also, shown in FIG. 1 is an air detector 40 provided in a proximal position (upstream) from the motor unit 28 along the intake tube 10 to warn medical personnel of an empty supply container or a large bubble in the infusion set.

In addition to these elements; the enteral feeding pump 20 of the present invention includes a pair of pressure sensors 50. In a preferred embodiment, two pressure sensors 50a and 50b are disposed along the pump tubing segment 16 adjacent the intake/output tubes to 1) ensure that the tubes are properly mounted in the pump 20; 2) monitor any changes in viscosity which are significant enough to alter the amount of liquid moved by each rotation or partial rotation of the rotor 30; and 3) detect any occlusions in the intake tube 10 or the output tube 14 of the delivery set 8. A retention plate 54 (FIG. 1) is attached to the housing 24 by a screw 58 to hold the pressure sensors 50a and 50b in place.

While the pressure sensor system of U.S. Pat. No. 5,720, 721 Was a significant improvement over the art, it does have limitations. Specifically, the pressure sensors are relatively expensive and the accuracy depends on the proper loading of the tube in the pump the air detector used ultrasonic energy and ultrasonic sensors are relatively expensive. Furthermore, as the health care professional or patient loaded the pump, he or she could effect the relative stretching of the tube as it was wrapped around the rotor of the pump. This, in turn, could effect the strain detected by the pressure sensors.

Figure 1B:
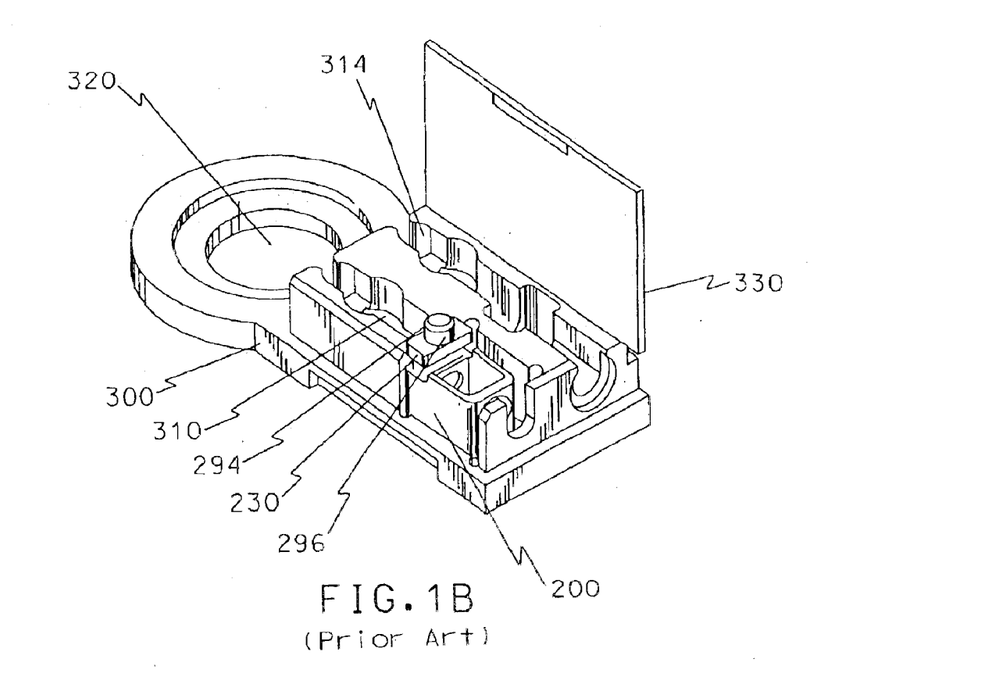
FIG. 1B shows a top view of a top of an enteral feeding pump housing and a pinch clip occluder formed in accordance with the principles of the prior art.

In addition to the above, the pump required some sort of anti free flow mechanism to prevent solution from running through the infusion set when the tube was not securely engaging the pump rotor. Thus, a pinch clip occluder, as shown in FIG. 1B at 96 was taught in U.S. Pat. No. 5,704,584. While the pinch clip occluder shown is highly effective, it is relatively expensive compared to the cost of the infusion set.

Figures 2A, 2B:
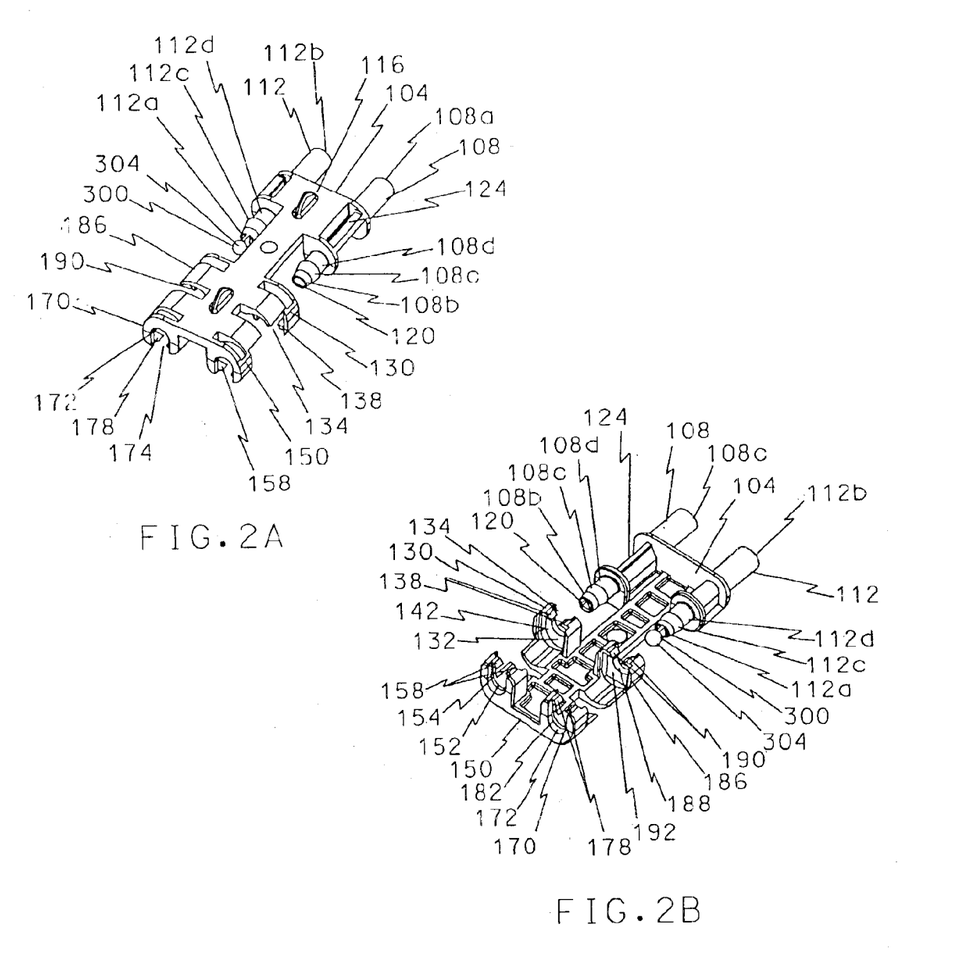
FIG. 2A shows a top perspective view of a feeding set adaptor configured in accordance with the principles of the present invention.
FIG. 2B shows a bottom perspective view of the feeding set adaptor shown in FIG. 2A.

Turning now to FIGS. 2A and 2B there are shown a top perspective view and a bottom perspective view of a feeding set adaptor, generally indicated at 100, which improves upon the prior art. The feeding set adaptor has a connector portion 104 having a first connector 108 and a second connector 112. The first connector portion 104 also preferably has a small handle 116 which can be used to pull the feeding set adaptor 100 from a pump if necessary.

The first connector 108, a functional proximal end 108a which engages the functional distal end of an inflow line (not shown) of an infusion set. The opposing end of the infusion line is typically disposed in communication with a fluid container which holds the solution being delivered to the patient. The first connector 108 will typically be approximately the same diameter as the inflow tube, and the inflow tube is mounted on the first connector by being stretched over the distal end 108a of the connector.

The first connector 108 also has a functional distal end 108b. The distal end 180b is preferably configured with an annular barb 108c and a neck portion 108d positioned proximally from the annular barb. The annular barb 108c and neck portion 108d are used to secure a pump engagement portion of the infusion set, which is discussed below regarding FIG. 2C. As shown in FIG. 1, the distal end 108b of the first connector 108 has conduit 120 which is generally triangular.

Disposed within the first connector 108 is a sample cell 124. As will be discussed in additional detail below, the sample cell 124 is used in conjunction with an optical sensor (not shown) to optically determine the presence of air bubbles within the conduit 120. The sample cell 124 is preferably triangular and has sidewall which are offset from one another at an angle of between about 47–70 degrees. In a presently preferred embodiment, the sample cell 124 is made with a wall which forms an equilateral triangle with two sidewalls being disposed at an angle of about 50 to 60 degrees. Such an angle allows light emitted from the optical sensor to be refracted in a first direction if the conduit 120 is filled with liquid, and a second direction if the conduit has any appreciable amount of air. The refracted light, or relative absence thereof, indicates the relative size of the air bubble. A more detailed discussion regarding bubble detection is found in U.S. patent application Ser. No. 09/836,840, now U.S. Pat. No. 6,531,708, which is expressly incorporated herein.

Disposed functionally distally (i.e. downstream) from the distal end 108b of the first connector 108 is a first tube engagement member 130. The first tube engagement member 130 preferably includes a wall 132 having generally U-shaped opening 134 which is sized to receive the pump engagement portion of the infusion set.

The first tube engagement member 130 also preferably includes a pair of flanges 138 which extend inwardly to partially obstruct the opening and to form a recess which receives a collar (see FIG. 2C) of the pump engagement portion of the infusion set.

Figure 2C:
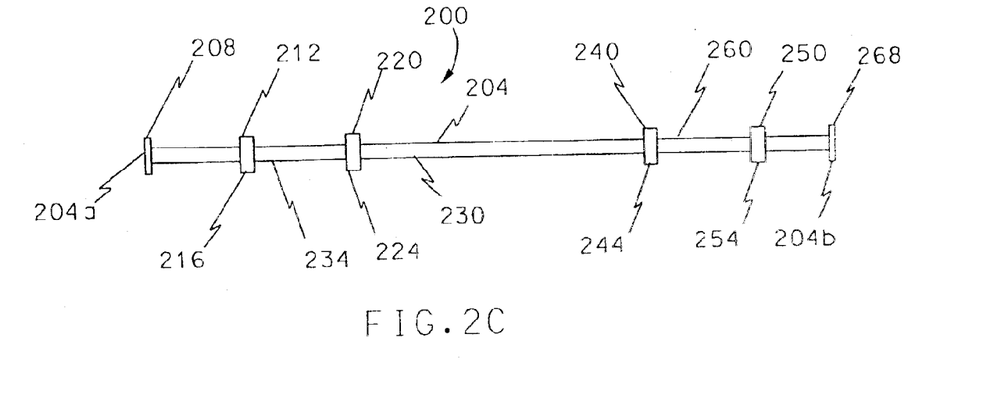
FIG. 2C shows a side view of the pump engaging portion of the infusion set.

The pump engagement portion of the infusion set, which is generally indicated at 200 in FIG. 2C includes an elongate tube portion 204. The tube portion 204 is preferably a flexible tube made from a medical grade material, such as silicone. Such tubes are commonly used in enteral feeding pumps.

Unlike most enteral feeding pump tubes, however, the tube portion 204 has a first fitting 208 disposed at a functionally proximal end (i.e. upstream). The first fitting 208 is preferably used by a machine to secure the tube portion 204 and to attach a proximal end 204a of the tube to the distal end 108b of the first connector 108.

Disposed distally from the first fitting 208 is a first abutment member 212, which is preferably in the form of a collar 216. (In light of the present disclosure, those skilled in the art will appreciate that numerous other abutment configurations could be used to secure the tube portion 204 as described). The abutment member 212 in particular, and the collar 216 specifically, are designed to nest in the recess 142 against the wall 132 of the first tube engagement member 130. When nested in the recess, the tube portion 204 which is proximal to the collar 216 is held taut between the first tube engagement member 130 and the first connector 108.

When the pump engaging portion 200 of the infusion set is attached to the distal end 108b of the first connector 108, it is stretched slightly until the collar 216 is slightly passed the flanges 134 of the first tube engagement member 130. The tube portion 204 is then moved between the flanges 134 and the tube released so the contraction of the tube pulls the collar 216 into the recess 142.

Disposed distally from the first tube engagement member 130 is a second tube engagement member 150. As with the first tube engagement member 130, the second tube engagement member preferably includes a wall 152 with a generally U-shaped opening 154 which is sized to receive the pump engagement portion of the infusion set.

The second tube engagement member 150 also preferably includes a pair of flanges 158 which extend inwardly to partially obstruct the opening and to form a recess 162 which receives an abutment member 220, which is preferably in the form of a collar 224 (FIG. 2C). (Those skilled in the art will appreciate that other abutment members such as arms, nubs or flanges could also be used). As shown in FIG. 2B, the recess 162 preferably faces the recess 142 in the first tube engagement member and works with the collar 224 to prevent the portion of the tube portion 204 disposed proximally adjacent to the collar from being stretched to any significant degree when the central working portion 230 of the pump engaging portion 200 of the infusion set. Likewise, when the pump rotor rotates, the stretching of the tube portion 204 proximally from the collar 224 is minimized.

Because the proximal collar 216 prevents proximal movement and the distal collar 224 prevents distal movement, the portion 234 of the tube disposed therebetween is held against movement, this portion forms a relatively isolated monitoring portion 234.

To properly determine the flow through an infusion set, and to properly determine the presence of occlusions in an infusion set, it is advantageous to monitor pressure within the infusion set. This can be accomplished either by pressure sensors, such as those discussed in U.S. Pat. No. 5,720,721, or by an optical detector as discussed in co-pending U.S. patent application Ser. No. 09/836,852, now U.S. Patent No. 6,523,414. As is explained more fully in the co-pending application, the pressure in the infusion set can be determined by having the tube occlude light in an optical sensor. As the tube expands due to increased pressure or contracts due to a vacuum caused by occlusions, etc., the amount of light which is received by the optical sensor changes, thereby indicating the change in pressure in the tube.

Using the diameter of the tube to determine pressure can provide highly accurate readings. However, the accuracy of such readings is diminished if the tube is being stretched inconsistently because having the tube under tension will change the extent to which it expands and contracts due to pressure changes. This is resolved in the present invention by the first and second tube engagement members 130 and 150 and the abutment members 212 and 220 (collars 216 and 224). These structures interact so that the monitoring portion 234 is held relatively unstretched, regardless of tension from either side. Because most of the tension will occur due to loading the central working portion 230 of the pump engagement portion 200 of the pump rotator, the second tube engagement member 150 is more critical than the first pump engagement portion. Thus, it will be appreciated that the first pump engagement portion 130 could be omitted while maintaining most of the benefits of the present invention.

The feeding set adaptor 100 also includes a third tube engagement member 170. The third tube engagement member preferably includes a wall 132 defining a generally U-shaped opening 174 which is sized to receive the pump engagement portion of the infusion set. The third tube engagement member 170 also preferably includes a pair of flanges 178 which extend inwardly to partially obstruct the opening and to form a recess 182 which receives an abutment member 240, which is preferably in the form of a collar 244 (FIG. 2C).

As shown in FIG. 2B, the recess 182 preferably faces in the same direction as the recess 162 in the second tube engagement member 150. When the pump engaging portion 200 of the infusion set is properly loaded, the collars 224 and 244 are disposed in recesses 162 and 182. This substantially isolates the central working portion 230 and prevents rotation of the pump rotor from causing tension either upstream or downstream from the collars 224 and 244, respectively.

The feeding set adaptor 100 further comprises a fourth tube engagement member 186. The fourth tube engagement member 186 preferably includes a wall having a generally U-shaped opening 188. A pair of flanges 190 are disposed adjacent the U-shaped opening to partially obstruct the opening and to form a recess 192. The pump engaging portion 200 of the infusion set includes an abutment member 250 in the form of a collar 254 which is configured to nest in the recess 192.

The recess 192 of the fourth tube engagement member 186 faces the same direction as first tube engagement member 130 and the third and fourth tube engagement members act together in the same manner as the first and second engagement members to isolate a second monitoring, portion 260 on the tube 204. Thus, the infusion pump is able to optically monitor both the upstream pressure between the first and second engagement members 130 and 150, and the downstream pressure between the third and fourth engagement members. Thus, the pump can readily determine if an occlusion in the infusion set is inhibiting delivery of solution to the patient.

The feeding set adaptor 100 also includes an anti-freeflow mechanism 300. As shown in FIGS. 2A and 2B, the anti-freeflow mechanism 300 is in the form a small ball 304 which is attached to the proximal (i.e. upstream) end 112a of the second connector 112 by a small wall 308. The wall 308 is configured to provide minimal resistance to flow of liquid into the proximal end 112a of the second connector 112.

In order to prevent freeflow through the infusion set, the anti-freeflow mechanism 300 is inserted into the distal end 204b of the tube portion 204. The tube portion 204 is then advanced until the distal end 204b passes over an annular barb 112c and rests on the neck 112d of the second connector 112. A second fitting 268 on the tube portion 204 is typically used so that a machine can readily mount the distal end 204b of the tube portion 204 on the proximal end 112a of the second connector 112.

Once, the tube is in place, the small ball 304 will prevent solution flow through the tube portion 204 unless the solution is under sufficient pressure. Thus, the small ball 308 will prevent flow through the tube portion 204 if the solution is simply subject to gravity. However, if the solution is placed under sufficient pressure, the flexible material (typically silicone) of the tube portion 204 will expand and allow solution to flow past the small ball 308. This is accomplished as the pump drives solution through the infusion set. If the pump is not properly engaging the central working portion 230 of the tube portion 204, there will not be enough pressure to bypass the anti-freeflow mechanism 300. In other words, unless the pump is in control of the fluid flow, no fluid will flow through the infusion set and a freeflow situation will not develop.

While the workings of the anti-freeflow mechanism 300 are discussed in additional detail below, numerous different embodiments of anti-freeflow mechanisms which can be used with the present invention are discussed in U.S. patent application Ser. No. 09/569,332, now U.S. Pat. No. 6,595,950 and U.S. patent application Ser. No. 09/836,850, both of which are expressly incorporated herein.

Once the solution in the tube portion 204 has been driven past the anti-freeflow mechanism 300, the solution passes into the proximal end 112a of the second connector 112. The distal end (downstream) 112b of the second connector 112 is disposed in engagement with a patient portion of the infusion set (not shown). Typically, the patient portion of the infusion set is slid over the second connector 112 and retained in a frictional engagement. It can, however, be attached by other means.

Figure 3:
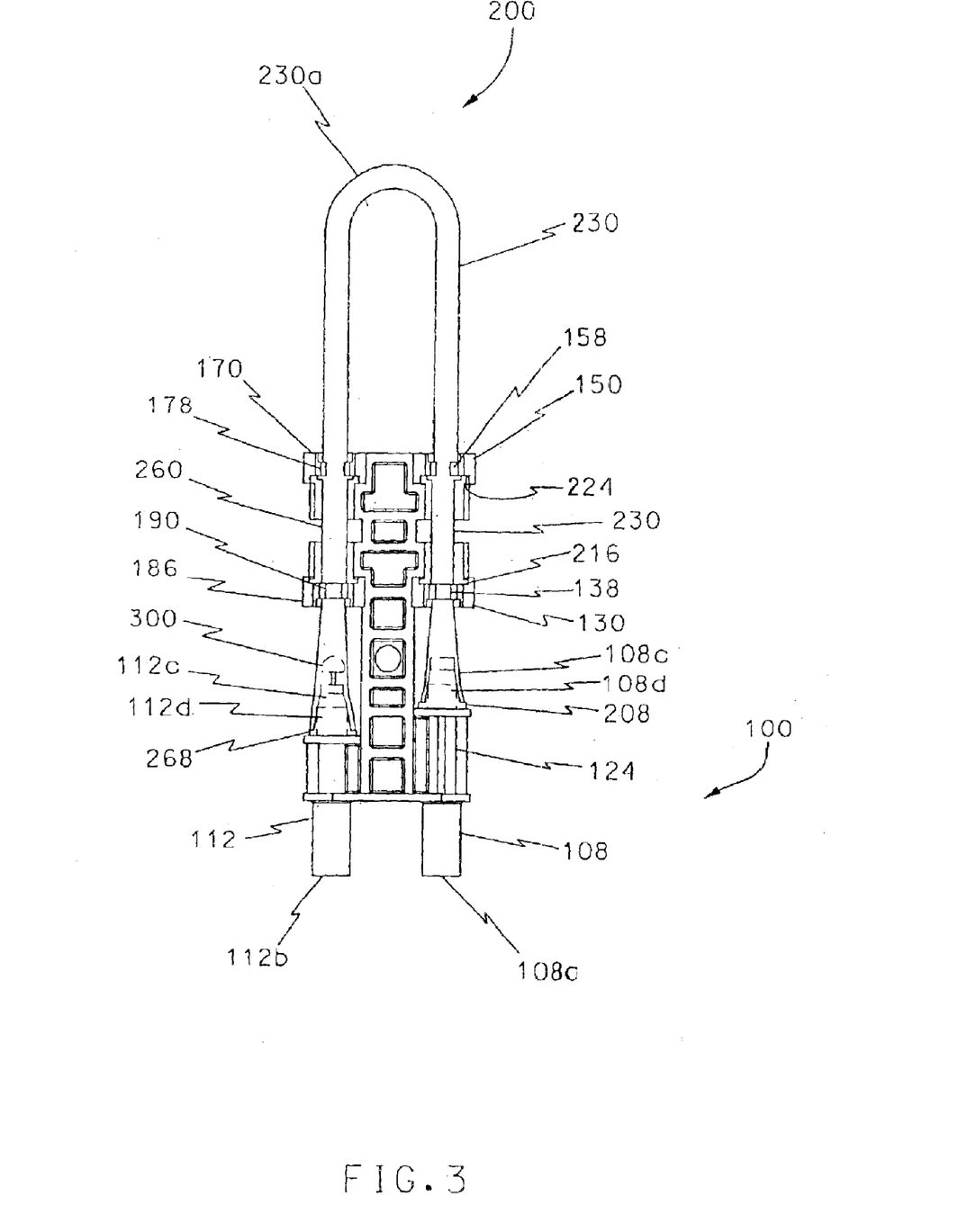
FIG. 3 shows a bottom view of an enteral feeding set adaptor having the pump engaging portion of the infusion set disposed therein for mounting on an infusion pump in accordance with the principles of the present invention.

Turning now to FIG. 3, there is shown a bottom view of an enteral feeding set adaptor 100 having the pump engaging portion 200 of the infusion set disposed therein for mounting on an infusion pump in accordance with the principles of the present invention. The central working portion 230 of the pump engaging portion 200 extends outwardly from the feeding set adaptor 100 in a loop.

In the prior art configurations, the portion of the infusion set which engages the pump rotor can be stretched unevenly as it is mounted on the pump. This can interfere with monitoring of pressure within the infusion set. Additionally, stretching the tube and wrapping it around the pump rotor can take some coordination.

In contrast, the feeding set adaptor 100 and pump engaging portion 200 of the infusion set is loaded by simply engaging the far side of the loop 230a against the pump rotor and pulling the feeding set adaptor 100 until it can be inserted in the pump. With such a configuration, the risk of the central working portion 230 being stretched unevenly is virtually eliminated. Additionally, it takes very little coordination to properly load the feeding set adaptor 100 in the pump. The user simply loops the end 230a of the looped central working portion 230 over the rotor and pulls back on the feeding set adaptor 100 until it is in alignment with a cavity on the pump, and releases the feeding set adaptor.

Figure 4:
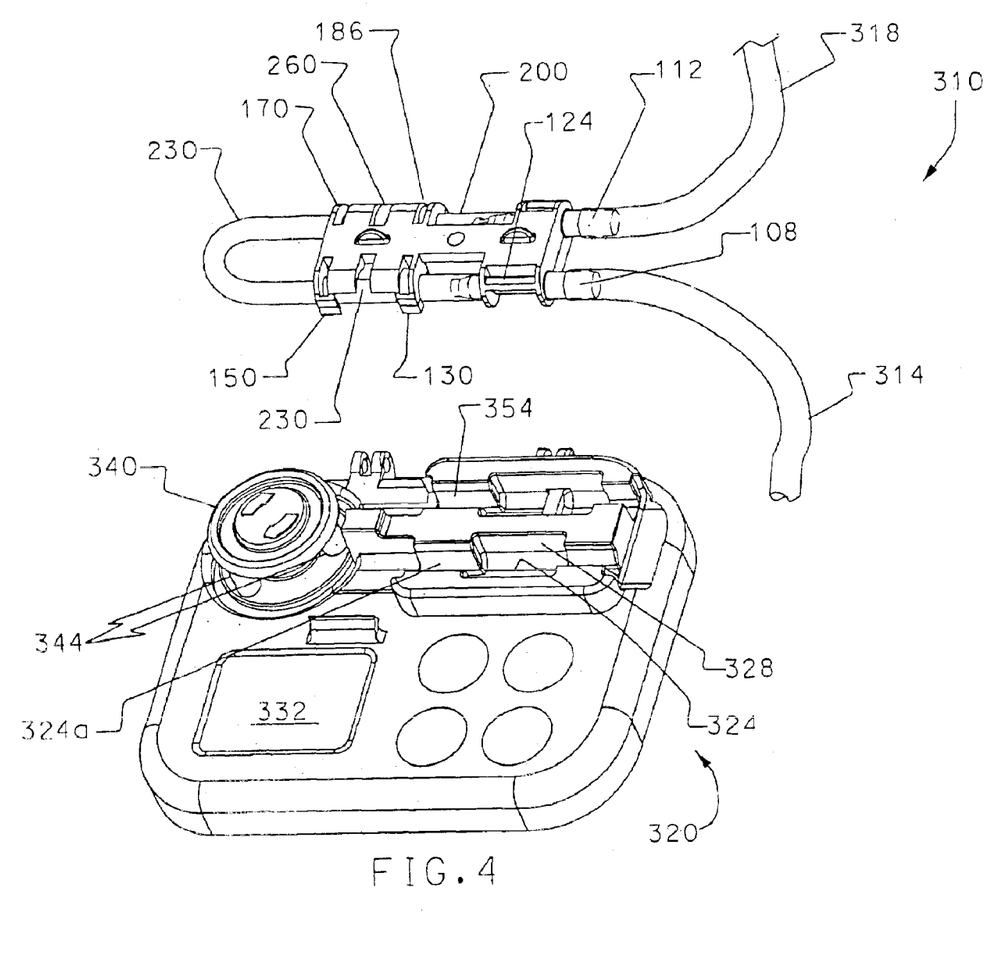
FIG. 4 shows a fragmented perspective view of an infusion set and a perspective view of a feeding set adaptor and an enteral feeding pump made in accordance with principle of the present invention.

Turning now to FIG. 4, there is shown a fragmented perspective view of an infusion set, generally indicated at 310 and a perspective view of a feeding set adaptor 100 and an enteral feeding pump, generally indicated at 320, made in accordance with principle of the present invention. The infusion set 310 includes an inflow tube 314 which is typically connected to a solution container (not shown), such as a plastic bag holding enteral feeding solution, and an outflow tube 318, which is generally connected to an adaptor (not shown) which engages a balloon catheter which traverses the abdominal wall of the patient.

The inflow tube 314 is connected to the pump engaging portion 200 of the infusion set 310 by the first connector 108. As discussed above, the solution passing through the inflow tube 314 and the first connector 108 passes through the sample cell 124. Due to the configuration of the feeding set adaptor 100, the sample cell 124 nests in a channel 324 of the infusion pump 320. A portion of the channel 324 defines a housing 328 which is preferably made of a generally translucent plastic. The housing 328 serves the dual purpose of protecting an optical sensor (not visible in FIG. 4) from liquids, and of refracting light which is emitted and received by various parts of the optical sensor.

As the solution passes through the sample cell 124, the optical sensor sends light through the housing 328 and sample cell 124. If liquid is in the sample cell 124, most of the light will travel in such a path that it is not reflected back to an optical detector. The sample cell 124 is specifically designed so that it always sends some light to the optical detector to provide an integrity check of the optical sensor. If a bubble is present, however, a light emitted by the optical sensor is refracted to the optical detector. The amount of light which is refracted gives a reliable indication of whether a bubble is present, and the size of the bubble. If the bubble exceeds desired thresholds, the pump 320 can generate an alarm. The alarm may be audible, or simply appear on a display screen 332 on the pump 320.

Once the solution has passed through the sample cell 124, it passes out of the first connector 108 and into the monitoring portion 230 of the pump engaging portion 200 of the infusion set 310. The monitoring portion 234 is disposed between the first and second tube engagement members 130 and 150, and is disposed in a distal section 324a of the channel 324. Disposed in the walls of the distal section 324a of the channel 324 is an optical sensor (not shown). The optical sensor sends light between an optical signal emitter and an optical signal detector. As the monitoring portion 234 of the tube is disposed in the distal section 324a of the channel 324, it is positioned to partially obstruct the light flow between the optical signal emitter and the optical signal detector.

The diameter of the monitoring portion 234 changes as pressure changes within the tube. The change in diameter of the monitoring portion 234 changes the amount of light which is detected by the optical detector and allows the pump 320 to determine pressure within the monitoring portion without direct contact. For example, if the inflow line 314 of the infusion set 310 were to be kinked or otherwise occluded, flow through the inflow line would be reduced. As the pump rotor 340 of the infusion pump 320 rotates, it will develop a vacuum upstream from the rotor. Because the inflow line 314 is occluded, the vacuum created by the rotation of the rotor 340 will be greater in magnitude and will remain longer than if flow through the inflow tube were not obstructed.

The vacuum will cause the monitoring portion 234 of the pump engaging portion 200 to collapse to a greater degree and remain in a collapsed state for a longer period of time. The optical sensor detects the collapse because more light will be detected by the optical detector and for a longer period of time. The pump 320 monitors the readings of the optical sensor. If the readings of the optical detector fall outside of a predetermined range, the pump 320 will generate an alarm indicating the presence of an occlusion. It may also automatically stop the pump 320 until the occlusion situation has been resolved. A more detailed discussion of the interaction between the optical sensor and the monitoring portion 234 of the infusion set 310 is set forth below. Additionally, co-filed U.S. patent application Ser. No. 09/836,852, now U.S. Pat. No. 6,523,414 contains a detailed discussion of numerous different applications of such a pressure sensor and is expressly incorporated herein.

As the solution passes out of the monitoring portion 234, it passes into the central working portion 230 of the pump engaging portion 200 of the infusion set 310. The central working portion 230 is engaged by a plurality of rollers 344 on the pump rotor 340. As the rotor 340 rotates, the rollers 344 pinch off sections of the tube and advance theoretically known volumes of solution with each rotation. (The actual volumes moved are partially dependent on the pressures on the solution both upstream and downstream from the rotor 340). By controlling the number of rotations of the rotor 340, and making modifications for detected pressures, the pump 320 can deliver a known volume of solution to the patient.

Once the solution has been moved downstream of the rotor 340, it passes into the second monitoring portion 260 which is disposed between the third and fourth tube engagement portions 170 and 186. The second monitoring portion 260 rests in a channel 354 in the pump 320 which is preferably disposed parallel to channel 324. The channel 354 also has an optical sensor which functions in substantially the same manner as the sensor discussed in association with the monitoring portion 234. The only significant difference between the two is that which the monitoring portion 234 will generally collapse due to vacuum created by the pump rotor 340 and upstream occlusions, the second monitoring portion 260 will generally expand due to solution being forced down stream by the pump rotor 340 and any occlusions downstream which inhibit the downstream flow of solution.

Once the solution passes out of the second monitoring portion 260, it must flow around the anti-freeflow device 300. As mentioned above, gravity alone is insufficient to develop flow around the anti-freeflow device 300. However, the rotation of the pump rotor 340 pushes solution downstream with sufficient force that the tube 204 adjacent the anti-freeflow device will expand and create a channel around the ball 304, thereby allowing the solution to flow down stream to the patient.

Once past the anti-freeflow device 300, the solution flows through the second connector 112 and into the outflow portion 318 of the infusion set 310 which delivers the solution to the patient.

Figure 5:
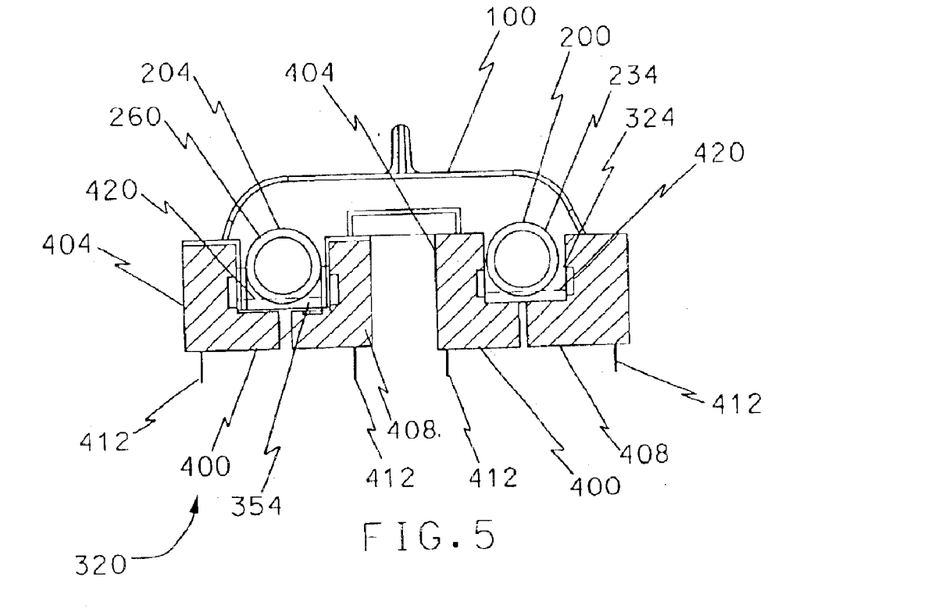
FIGS. 5 and 5A show close-up, cross-sectional views of the adaptor, flexible tubing and portion of the enteral feeding pump relating to the pressure monitoring mechanism associated with feeding set adaptor.
Figure 5A:
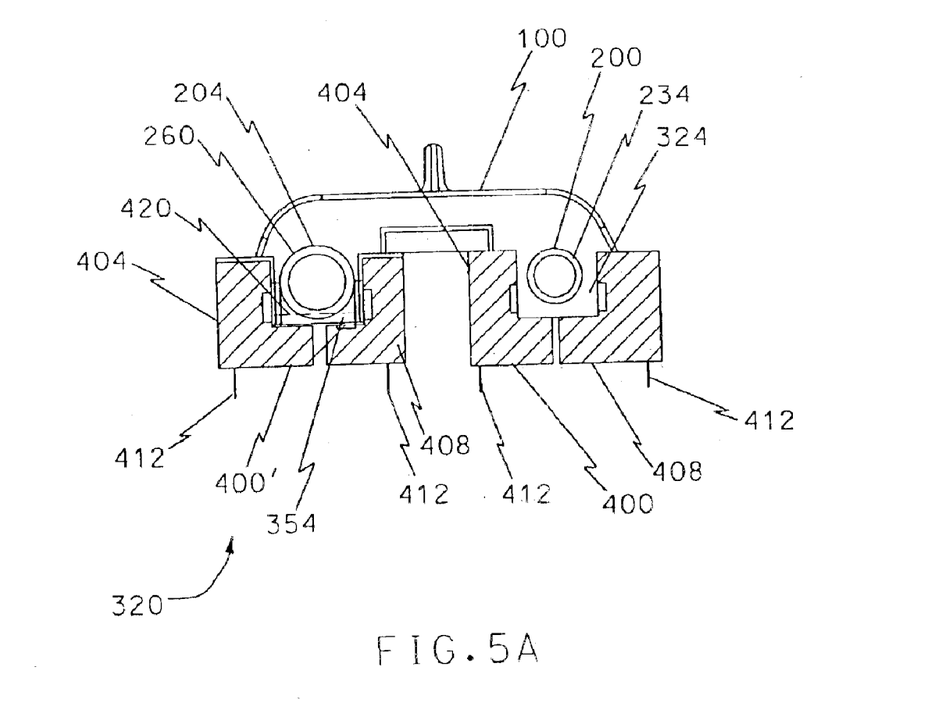

Turning now to FIGS. 5 and 5A, there are shown close-up, cross-sectional views of the feeding set adaptor 100, flexible tubing 204 of the pump engaging portion 200 and a portion of the enteral feeding pump 320 relating to the pressure monitoring mechanism associated with feeding set adaptor. The enteral feeding pump 320 has two channels 324 and 354 which receive the feeding set adaptor 100.

As shown in FIGS. 5 and 5A, the monitoring portion 230 of the flexible tubing 204 of the pump engaging portion 200 is disposed in the first channel 324. Disposed on opposing sides of the first channel 324 is an optical sensor 400. The optical sensor includes a optical signal emitter 404 and an optical signal detector 408. Each is provided with leads 412 for communication with the enteral feeding pump.

In response to an electrical signal from the pump 324, the optical signal emitter 404 emits light energy, indicated by dashed line 420. Those skilled in the art will appreciate that various wavelengths of light may be used. Currently, it is anticipated that infrared light will be preferred.

The flexible tube 204 forming monitoring portion 230 is positioned to obstruct some of the light. The extent to which the light is obstructed, of course, depends on the diameter of the flexible tube 204 in the monitoring portion 230. This diameter, depends on the pressure within the tube. Thus, by monitoring the amount of light which is obstructed, the voltage or other readings of the sensor correlates with the pressure inside of the tube.

In a preferred embodiment, the flexible tube 204 forming the monitoring portion 230 is disposed so that it always obstructs some light, but does not obstruct all light flow between the optical signal emitter and the optical signal detector. This can be used to verify the integrity of the sensor and proper loading of the tubing. If the optical signal detector 408 gives the maximum voltage reading, the tubing 204 is not loaded properly. If, in contrast, no optical signal is received by the optical signal detector 408, the sensor 400 is defective and must be serviced or replaced.

Turning specifically to FIG. 5A, there is shown a view similar to that of FIG. 5. However, with respect to the monitoring portion 230, the diameter of the tube 204 has decreased. This typically occurs with each rotation of the pump rotor (FIG. 4) as a temporary vacuum is created as solution is forced through the infusion set. The extent of the vacuum and its duration, however, is related to the presence of occlusions, and/or the viscosity of the solution. The sensor 400 detects the extent of the reduced diameter of the tube 204 in the monitoring portion 230 by the amount of light received by the optical signal detector 408. The optical sensor 400 is thereby able to determine the negative pressure within the tube. The pump 320 is then able to make adjustments to rotor rotations to ensure accurate volume delivery. It can also detect an occlusion that should be resolved and generate an alarm.

The pump 320 also has a second optical sensor 400' which is disposed along the second monitoring portion 260 which is down stream from the pump rotor (FIG. 4). The sensor 400' has an optical signal emitter 404 and an optical signal detector 408 which have leads 412 for communicating with the pump. The sensor 400' operates in substantially the same manner as the optical sensor 400 and is therefor not discussed in detail.

One difference between the practical applications of the sensor 400' and sensor 400 is that, because the sensor 400' is downstream, the sensor 400' will detect pressure increase in the second monitoring portion 260 with each rotor rotation, instead of the pressure decreases associated with the first monitoring portion 230. Thus, as the rotor (FIG. 4) rotates, the pressure in the second monitoring portion 260 will increase. As shown in FIG. 5A, the increase in pressure causes the diameter of the second monitoring portion to increase and decreasing the amount of light received by the optical signal detector 408.

The sensor 400' and monitoring portion 260 can be configured in a variety of ways to achieve the goals of the present invention. In a preferred configuration, the tube 204 is positioned within the sensor such that it will always occlude some light, but will never fully occlude all light from the optical signal emitter 404 to the optical signal emitter 408. Thus, a full voltage reading indicates that the tube 204 forming the monitoring portion 260 is not properly loaded. A zero reading indicates that the sensor 400' has malfunctioned and must be serviced or replaced.

Between the two extremes is a range of values which correlate with acceptable pressures which the pump 320 can use to ensure accuracy in volumetric delivery. This is also a threshold which indicates a pressure which exceeds acceptable pressure in the infusion set. If the threshold is surpassed, the pump 320 will generate an alarm and warn the user that the infusion set is obstructed.

Those skilled in the art will appreciate that the tube 204 and sensor 400' could be disposed in communication such that the threshold pressure occludes all light and therefore generates an alarm. While such a configuration meets the requirements of generating an alarm and/or shutting off the pump 320 when the pressure is too high, it has the disadvantage of not distinguishing between a faulty sensor in the pump and an unacceptably high pressure in the infusion set.

Those skilled in the art will also realize that numerous modifications could be made to the presently preferred embodiment disclosed herein. The sensors need not be disposed adjacent each other and could be disposed in other locations along an infusion set.

Figure 6:
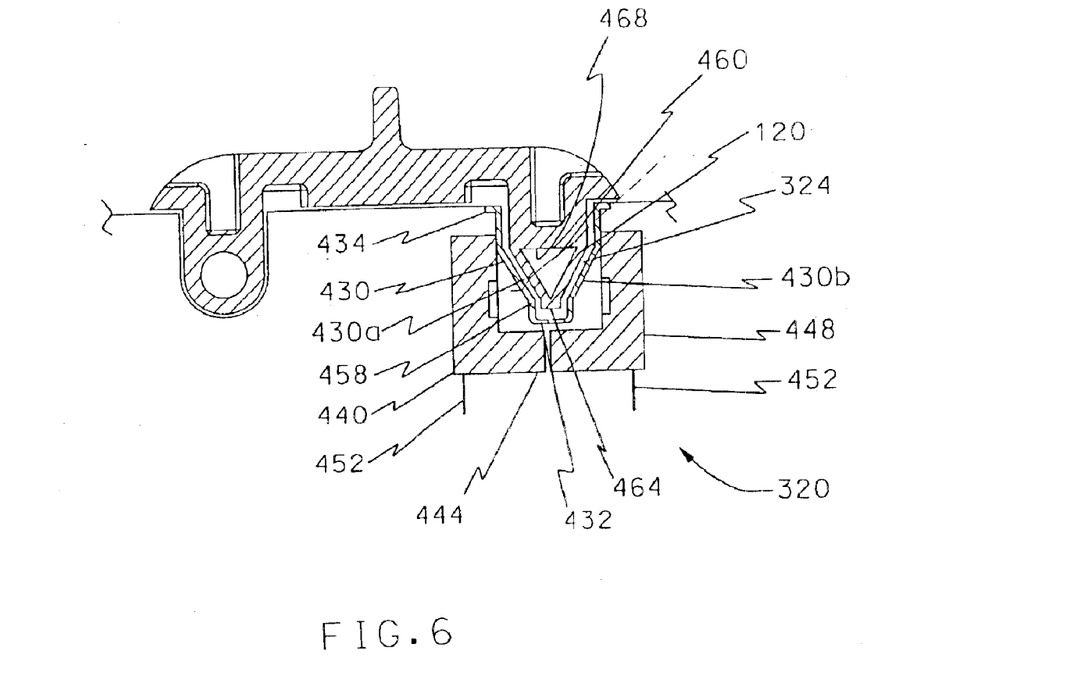
FIGS. 6 and 6A show a close-up, cross-sectional view of the adaptor and the enteral feeding pump portions relating to the detection of air bubbles passing through the infusion set.
Figure 6A:
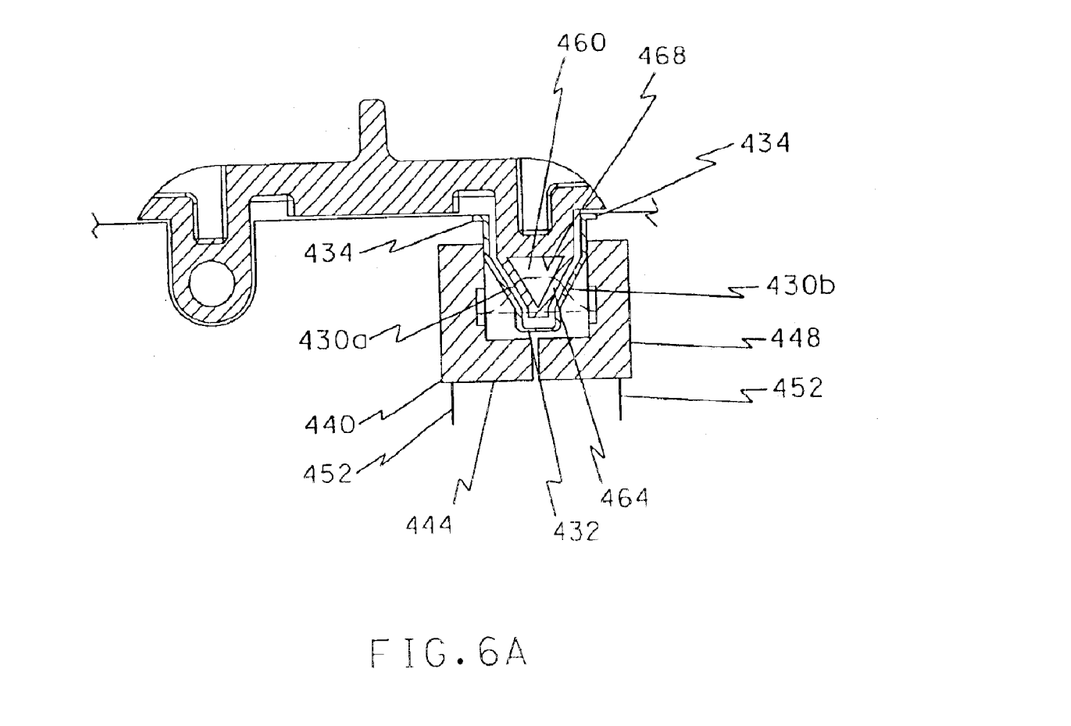

FIGS. 6 and 6A show a close-up, cross-sectional view of the adaptor and the enteral feeding pump portions relating to the detection of air bubbles passing through the infusion set. Specifically, the sample, cell 124 is disposed in the channel 324 of the pump. The channel 324 has a portion 324b which is defined by a sloped housing 430. The sloped housing 430 is preferably formed of a clear plastic, such as ABS and has walls 430a and 430b which are offset from one another at an angle of between about 45–100 degrees (most preferably about 60 degrees), and preferably between 40 and 67.5 degrees from horizontal, and a base 432. The housing also preferably has a flanged portion 434. The housing 430 helps both with bubble detection as explained below, and prevents water or other hazzards from entering the pump 320.

Disposed adjacent the housing 430 is an optical sensor 440. The optical sensor 440 has an optical signal emitter 444 and an optical signal detector 448 which are disposed on opposing sides of the housing 430. Leads 452 are provided for the optical sensor 440 and pump 320 to send electronic signals to one another.

The sample cell 124 is placed in the channel 324 so that it is spaced away from the housing 430 slightly and forms an air chamber 458 between the sample cell and housing. While it is preferred that the conduit 460 formed by the sample cell 124 has a cross-section which forms an inverted equilateral triangle and the sample cell 124 preferably has two walls disposed at 60 degrees from one another, the walls defining the conduit need not form a triangle. As shown in FIG. 6, the walls have a base 464 which is formed at the bottom of the inverted triangle. Additionally, the top wall 468 could be curved or vaulted to provide the conduit with a diamond shape. Also, as set forth in more detail in U.S. patent application Ser. No. 09/836,840, numerous different configurations can be used. It is most desirable, however, that the sidewalls be disposed at an angle less than normal to the plane along which the light is emitted to refract the light back to an optical detector when air is present in the sample cell.

In use, light is emitted by the optical signal emitter 444 and is refracted by a sidewall of the housing 430 and again by the air of the air chamber 458. The light is again refracted as it enters into the sidewall 430a of the housing. If the conduit 460 is filled with solution, the light undergoes very little refraction as it passes from the sidewall 430a of the housing 430 into the solution. Thus, the light travels in a generally straight path which prevents the light from contacting the optical signal receiver 448 as shown by the dashed line in FIG. 6.

If, however, the conduit 460 is filled with air, the difference indices of refraction of the plastic sample chamber 124 and the air in the conduit 460 causes the air to be refracted to a much greater degree as shown by the upper dashed line in FIG. 6A. The light is then refracted again as it passes from the air in the conduit to the opposing sidewall 430b, through the air chamber 458 and through the housing 430. The refraction is such that the light is directed to the optical signal detector 448. If an air bubble is present in the conduit 460, it will direct an increased amount of light to the optical signal detector 448. The amount of light refracted to the optical signal detector 408 is proportional to the size of the air bubble. Thus, the voltage reading obtained from the optical signal detector 448 is proportional to the size of the bubble.

The base 464 of the sample cell 124 assists in the important role of integrity checking the optical sensor 440. The base 464 is positioned so that it will always allow some light through to impact the optical signal detector 448 as shown by the lower dashed line in FIG. 6A. Thus, if the optical signal detector 448 indicates a reading of zero, an alarm can be generated indicating that the sensor 440 has failed. Likewise, the refraction of light is controlled so that too high of a reading indicates that the sample cell 124 has not been properly loaded in the channel 324.

Figure 7:
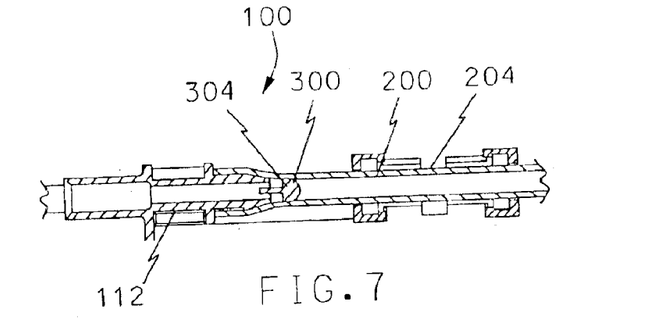
FIGS. 7 and 7A show close-up, cross-sectional views of the adaptor and infusion set relating to the anti-freeflow mechanism of the present invention.
Figure 7A:
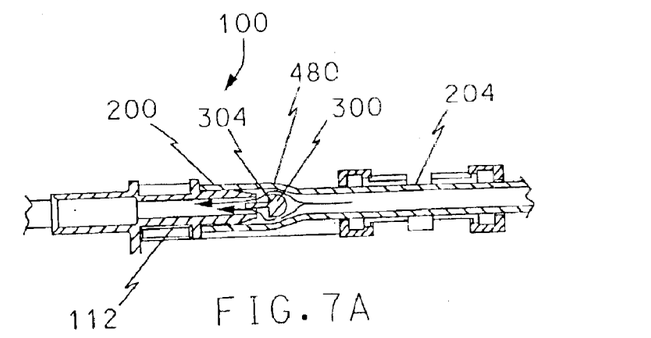

Turning now to FIGS. 7 and 7A, there are shown close-up, cross-sectional views of the feeding set adaptor 100 and the pump engaging portion 200 of the infusion set 310 as they relate to the anti-freeflow mechanism 300 of the present invention. It is important to prevent an infusion set from providing uncontrolled solution to the patient. While many enteral feeding systems have roller clamps or other pinch clip occluders, most devices do not affirmatively prevent fluid flow when the pump is not controlling the flow. In contrast, the anti-freeflow mechanism 300 only allows fluid flow when the pump is actively driving solution through the system.

The anti-freeflow mechanism shown in FIGS. 7 and 7A is a small substantially ball-shaped member 304 which is sized slightly larger than the inside diameter of the flexible tube 204 which forms the pump engaging portion 200 of the infusion set 310. As such, the ball-shaped member 304 prevents fluid flow under gravity pressures. If, however, a pressure well above that caused by gravity is developed in the flexible tube 204, the flexible tube will expand and develop a channel 480 about the exterior of the ball-shaped member 304. (It will be appreciated that other shapes may also be used).

The channel 480 is opened each time the pump rotor drives solution through the pump engaging portion 200 of the infusion set 310 and allows solution to flow downstream. Unlike other clamps which are manually controlled or which open by closing of the pump housing, the configuration is advantageous because it will not allow a freeflow condition to develop, even if the feeding set adaptor 100 is properly mounted in the pump 320 and the pump engaging portion 200 of the infusion set 310 has simply been pulled out of engagement with the pump rotor.

Figure 7B:
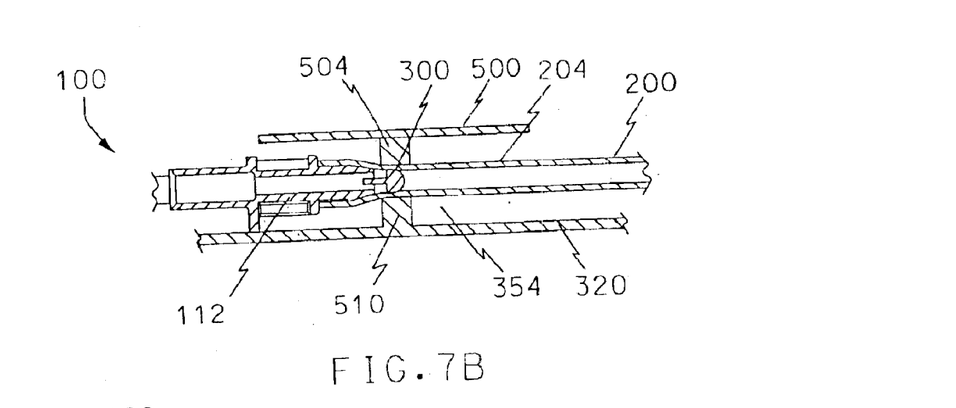
FIG. 7B shows a close-up, cross-sectional view of the adaptor, infusion set and enteral feeding pump providing an alternate embodiment of the anti-freeflow mechanism of the present invention.

Turning now to FIG. 7B, there is shown a cross-sectional view of the adaptor 100, pump engaging portion 200 of the infusion set 310 and enteral feeding pump 320 providing an alternate embodiment of the anti-freeflow mechanism of the present invention. While the embodiment discussed with respect to FIGS. 7 and 7A is presently preferred, there may be situations in which it is not desired to force the solution to open a channel around the anti-freeflow mechanism. In such situations, the channel can be opened by interaction of a pump cover 500, the anti-freeflow mechanism 300 and the channel 354 of the pump 320. The cover 500 preferably has an engagement member 504 which is configured to forcefully engage the flexible tube on the opposite side of the tube from the anti-freeflow mechanism. The channel 354 also may have a stop 510 which engages the outside of the flexible tube 204 opposite the anti-freeflow mechanism 300.

As the flexible tubing 204 gets compressed between the engagement member 504 and the anti-freeflow mechanism 300 and between the stop 510 and the anti-freeflow mechanism, the flexible tubing will bow outwardly along the sides of the anti-freeflow mechanism 300 and form channels for the solution to flow around the anti-freeflow mechanism. Thus, once the cover 500 is closed and secured, solution flow passed the anti-freeflow mechanism 300 can occur regardless of whether the pump rotor 340 is properly engaging the pump engaging portion 200 of the infusion set 310.

Figure 7C:
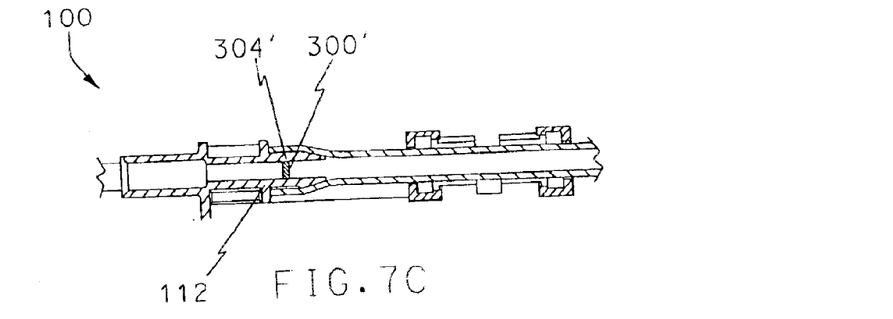
FIG. 7C shows a close-up, cross-sectional view of yet another embodiment of the anti-freeflow mechanism of the present invention.

Turning now to FIG. 7C, there is shown a close-up, cross-sectional view of yet another embodiment of the anti-freeflow mechanism 300' of the present invention. Instead of using a ball-shaped member 304 inside of the tube, the embodiment shown in FIG. 7C shows a flap 304' which is disposed in the connector 112. The flap is configured to substantially prevent fluid flow through the connector if pressures are equal to or less than typically encountered due to gravity. If a desired pressure threshold is passed, the flap 304' is forced open and allows solution to flow down stream. Those skilled in the art will appreciate that the flap 304' could be configured to remain open once deflected by the solution pressure, or could be mounted such that the flap 304' returns to its original position once the solution pressures are insufficient to hold the flap open.

Thus there is disclosed an improved feeding set adaptor. The adaptor enables the integration of the various functions discussed above, and provides improved pressure monitoring, anti-freeflow and bubble detection at a price well below the systems of the prior art. Additionally, the feeding set adaptor increases the ease of loading and unloading the tube engaging portion of the infusion set. While numerous different embodiments of the present invention have been disclosed, those skilled in the art will appreciate numerous modifications which can be made, without departing from the scope and spirit of the present invention. The appended claims are intended to cover such modifications.

What is claimed is:

1. A feeding system comprising:
    an infusion set comprising tubing configured for carrying a fluid, the tubing forming at least an inflow line, an outflow line, and a central pump engaging portion;
    a first connector configured for attachment to the inflow line of the infusion set and the central pump engaging portion of the infusion set;
    a second connector configured for attachment to the outflow line of the infusion set and the central pump engaging portion of the infusion set;
    an anti-freeflow mechanism disposed inside the central pump engaging portion of the tubing; and
    an optical pressure sensor disposed in optical communication with the infusion set the optical pressure sensor comprising an optical emitter and an optical detector disposed on opposite sides of a section of the infusion set.

2. A feeding system according to claim 1, wherein the anti-freeflow mechanism is attached to and spaced apart at a predetermined distance from one of the first connector and the second connector.

3. A feeding system according to claim 1, wherein the anti-freeflow mechanism comprises a generally ball-shaped member configured for disposition in the tubing of the infusion set.

4. A feeding system according to claim 3, wherein the ball-shaped member is attached to one of the first connector and the second connector and continually spaced away from the connector to which the ball-shaped member is attached so that a flow channel may be formed around the ball-shaped member and into the connector to which the ball-shaped member is attached.

5. The feeding system according to claim 1 wherein the central pump engaging portion extends between the first connector and the second connector.

6. The feeding system according to claim 5, wherein the anti-freeflow mechanism is disposed in one of the inflow line, pump engaging portion and outflow line.

7. The feeding system according to claim 6, wherein the anti-freeflow mechanism is attached to the second connector and disposed in the central pump engaging portion of the infusion set.

8. The feeding system according to claim 7, wherein the outside diameter of the anti-freeflow mechanism is slightly larger than the inside diameter of the pump engaging portion of the infusion set.

9. The feeding system according to claim 5, wherein the anti-freeflow mechanism is a generally ball-shaped member.

10. The feeding system according to claim 1, wherein the optical pressure sensor is configured to monitor the change in size of the infusion set tubing due to changes in pressure within the tubing.

11. The feeding system according to claim 10, wherein the central pump engaging portion comprises at least one protrusion configured to minimize movement of the central pump engaging portion when the pump engaging portion is worked by a pumping mechanism.

12. The feeding set according to claim 11, wherein the at least one protrusion comprises at least one annular ridge formed on the central pump engaging portion.

13. The feeding set according to claim 1, wherein the optical pressure sensor comprises an optical emitter is disposed on one side of a section of the central pump engaging portion and wherein the optical detector is disposed on the opposite side of the section of the central pump engaging portion such that the central pump engaging portion of tubing partially obstructs the flow of light from the emitter to the detector.

14. The feeding set according to claim 13, wherein the section of the central pump engaging portion adjacent the optical emitter and optical detector is sufficiently elastic to expand somewhat in response to changes in pressure within the tubing and thereby change the amount of light emitted from the emitter which strikes the detector.

15. The feeding set according to claim 1, further comprising an optical bubble detector.

16. The feeding set according to claim 15, wherein the optical bubble detector comprises a triangular conduit formed from a transparent material, an optical emitter disposed adjacent one side of the conduit, and an optical emitter disposed along the opposite side of the conduit such that light emitted from the emitter passes through the conduit and is received by the detector, and such that the presence of an air bubble in the conduit changes the amount of light received by the detector.

17. The feeding set according to claim 16, wherein the triangular conduit further comprises a portion having substantially parallel outer walls such that light passing through the portion of the conduit is not substantially refracted, thus allowing a portion of the light emitted from the emitter to be received by the detector regardless of the presence or absence of a bubble in the conduit.

18. The feeding system according to claim 1, wherein the optical sensor monitors pressure at a point along the central pump engaging portion.

19. A solution delivery system comprising:
    a feeding set comprising:

an infusion set comprising tubing configured for carrying a fluid and being attached to a first connector and a second connector, the tubing forming at least an inflow line, an outflow line, and a central pump engaging portion, the central pump engaging portion extending between the first connector and the second connector and wherein the central pump engaging portion comprises at least one monitoring portion for optically monitoring pressure within the infusion set and at least one abutment member configured for minimizing movement of the monitoring portion when the pump engaging portion is worked by a pumping mechanism;

a first connector configured for attachment to the inflow line of an infusion set and the central pump engaging portion of the infusion set;

a second connector configured for attachment to the outflow line of an infusion set and the central pump engaging portion of the infusion set;

an anti-freeflow mechanism disposed in communication with the one of the first connector and the second connector, the anti-freeflow mechanism being disposed inside the tubing; and a void disposed in the solution delivery system and configured for receiving the feeding set, the void comprising at least one tube engagement member, and wherein the abutment member of the pump engaging portion engages the tube engagement member of the solution delivery system to thereby limit movement of the pump engagement portion.

20. The solution delivery system according to claim 19, wherein the at least one tube engaging member defines a recess, and wherein the abutment member comprises a collar configured for resting in the recess.

21. The solution delivery system according to claim 19, wherein the at least one tube engagement member comprises a first tube engagement member and a second tube engagement member disposed adjacent to each other with the monitoring portion extending therebetween.

22. The solution delivery system according to claim 21, wherein the pump engagement portion has a first abutment member disposed to engage the first tube engaging member and a second abutment member disposed to engage the second tube engaging member, the two abutment members being spaced apart and a distance therebetween constituting the monitoring portion of the pump engaging portion of the infusion set.

23. The solution delivery system according to claim 21, wherein the at least one tube engagement member further comprises a third tube engagement member and a fourth tube engagement member disposed adjacent to each other, and the pump engaging portion of the infusion set forming a second monitoring portion extending between the third tube engagement member and the fourth tube engagment member.

24. The solution delivery system according to claim 19, wherein the at least one tube engaging member and the at least one monitoring portion comprise a first monitoring portion and at least one tube engagement configured for disposition upstream from a pump rotor, and a second monitoring portion and at least one tube engagement member configured for disposition downstream from a pump rotor.

25. A feeding set comprising:

an infusion set comprising tubing for carrying a liquid, the tubing comprising an inflow line, and outflow line, and a central pump engaging portion, and wherein the central pump engaging portion is formed with at least one protrusion configured for inhibiting movement of at least one portion of the central pump engaging portion when the central pump engaging portion is worked by a pump;

at least one connector configured for attaching two lines of the feeding set, an anti-freeflow mechanism disposed inside of the tubing of the infusion set; and a sample cell formed as part of the at least one connector and configured for detecting bubbles.

26. The feeding set according to claim 25, wherein the sample cell has a pair of side walls disposed at an angle between about 45 and 100 degrees from one another.

27. The feeding set according to claim 26, wherein the sample cell defines a conduit having at least two sides which are disposed at an angle of about 50 to 60 degrees from one another.

28. The feeding set according to claim 27, wherein the conduit has a cross-section which is an equilateral triangle.

29. The feeding set according to claim 25, wherein the conduit is configured such that a light beam entering an empty sample cell exits substantially parallel to the entering light beam, and a light beam entering a sample cell which is full of a liquid does not exit parallel to the entering beam.

30. The feeding set according to claim 25, wherein the conduit is configured such that a light beam entering a sample cell which is full of a liquid exits in a first direction, a light beam entering an empty sample cell exits in a second direction, and a light beam entering a conduit which is either partially full of a liquid or full of a liquid which contains bubbles therein exits in a third direction.

31. The feeding set according to claim 25, wherein the sample cell has a pair of outer walls which extend towards a point, and a generally linear base extending outwardly from the point and disposed to allow light to flow through the base with minimal refraction.

32. A solution delivery system comprising the feeding set according to claim 25, and further comprising a housing disposed adjacent to the sample cell.

33. The solution delivery system according to claim 32, wherein the housing is spaced apart from the sample cell so as to form an air chamber between the housing and the sample cell.

34. The solution delivery system according to claim 32, wherein the housing has a pair of sidewalls which are disposed at an angle of between about 45 and 100 degrees from one another.

35. The solution delivery system according to claim 34, wherein the housing further comprises a base disposed at an angle of about 50 to 60 degrees from each of the sidewalls.

36. A solution delivery system comprising the feeding set according to claim 25, and further comprising a optical sensor disposed to project light into the sample cell.

37. The solution delivery system according to claim 36, wherein the optical sensor comprises an optical signal emitter and an optical signal detector, and wherein the sample cell is disposed between the optical signal emitter and the optical signal detector.

38. The solution delivery system according to claim 36, wherein the sample cell is configured to direct more light emitted from the optical signal emitter to the optical signal detector when the sample cell is at least partially filled with air.

39. The feeding set adaptor of claim 25, wherein the anti-free flow mechanism is configured for disposition in the pump engaging portion of the infusion set.

40. The feeding set adaptor of claim 25, wherein the sample cell is formed integrally with one of the at least one connector and is generally rigid.

41. A method for preventing freeflow in an infusion set, the method comprising:

selecting a feeding set having a pump engaging portion, the feeding set further comprising a connector, a monitoring portion, at least one protrusion configured to inhibit movement of the monitoring portion and an anti-freeflow mechanism configured to selectively stop fluid flow through the infusion set; and disposing the anti-freeflow mechanism in the pump engaging portion of the feeding set at a fixed distance from the connector to selectively preclude fluid flow therethrough.

42. The method of claim 41, wherein the method further comprises selecting an anti-freeflow mechanism which is attached to one of the at least one connector.

43. The method of claim 41, wherein the method further comprises selecting an anti-freeflow mechanism which allows flow past the anti-freeflow mechanism when a predetermined pressure is generated by a pump.

44. The method of claim 41, wherein the method further comprises selecting an anti-freeflow mechanism which allows flow past the anti-freeflow mechanism when the tubing in which the mechanism is disposed is expanded radially.

45. The method of claim 41, wherein the method further comprises disposing an optical bubble detector in the feeding set.

46. The method of claim 45, wherein the method further comprises selecting a optical bubble detector with an optical emitter and an optical receiver spaced apart from each other, and wherein the optical bubble detector allows a first amount of light to reach the optical receiver when the detector is not placed between the emitter and the receiver, a second amount of light less than the first amount of light to reach the optical receiver when the detector is placed between the emitter and the receiver but a bubble is present in the detector, and a third amount of light which is less than the second amount of light to reach the optical receiver when the detector is placed between the emitter and the receiver and the detector is filled with a liquid.

47. The method of claim 45, wherein the method further comprises selecting an optical bubble detector which comprises a conduit with a triangular cross section.

48. The method of claim 45, wherein the method further comprises selecting an optical bubble detector which comprises a conduit with a generally triangular cross section having a base portion extending from one edge of the conduit, the base portion having parallel side walls and being configured to transmit a light beam without refracting the light beam.

49. A method for detecting air bubbles passing through an infusion set, the method comprising;

selecting a feeding set formed of tubing and consisting of at least an inflow line, and outflow line, and a pump engaging portion, and having a sample cell formed thereon and having at least one protrusion formed on the pump engaging portion for limiting movement of the pump engaging portion when worked upon by a pump;

passing solution through the sample cell; and disposing the sample cell in an optical signal such that light is refracted differently when air is present in the sample cell than when solution is present in the sample cell to thereby determine the presence of air.

50. The method according to claim 49, wherein the method comprises emitting the light in a plane and positioning the sample cell so that a sidewall of the sample cell is at an angle less than normal to the plane.

51. The method according to claim 49, wherein the method comprises passing the solution through a sample sell which has a triangular cross-section.

52. The method according to claim 49, wherein the method comprises passing light through a portion of the sample cell having walls which are disposed at an angle of between about 47 and 70 degrees so as to refract said light.

53. The method according to claim 49, wherein the method further comprises passing a quantity of light through the sample so that said quantity of light is not refracted or reflected by the contents of the sample cell.

54. The method of claim 49, wherein the at least one protrusion comprises at least one annular ridge.

55. The method of claim 49, wherein the method further comprises selecting a sample cell which further comprises an optical emitter and an optical detector.

56. The method of claim 55, wherein the method further comprises disposing the sample cell between the optical emitter and the optical detector.

57. The method of claim 55, wherein the method further comprises selecting a sample cell which directs more light towards the optical detector when a bubble is present in the cell.

58. The method of claim 55, wherein the method further comprises selecting a sample cell which directs some light towards the optical detector regardless of the contents of the sample cell.

59. The method of claim 49, wherein the method further comprises disposing an occluder in the feeding set tubing.

60. The method of claim 59, wherein the occluder further comprises a connector.

61. The method of claim 59, wherein the occluder prevents flow in the feeding set tubing until a pump generates a predetermined pressure within the feeding set.

62. A method for forming a feeding set, the method comprising:

selecting an infusion set having an inflow line and an outflow line;

connecting the inflow line to a first connector and the outflow line to a second connector;

disposing at least one protrusion on the tubing of the infusion set, the at least one protrusion being configured for inhibiting movement of at least one portion of the infusion set when the infusion set is worked upon by a pump; and disposing a flow restricting device inside the infusion set.

63. The method according to claim 62, wherein the method comprises selecting at least one of the first connector and the second connector with a flow restricting device formed integrally therewith, so as to selectively prevent flow in the infusion set when the flow restricting device is disposed therein.

64. The method of claim 62, wherein the method further comprises selecting a flow restriction device which occludes the lumen of the infusion set tubing, thereby requiring expansion of the tubing to allow flow around the flow restriction device.

65. The method of claim 62, wherein the method further comprises disposing an optical pressure sensor in the infusion set.

66. The method of claim 65, wherein the method further comprises disposing a portion of the infusion set tubing between an optical emitter and an optical detector.

67. The method of claim 66, wherein the method further comprises disposing at least one retaining wall adjacent the portion of the infusion set to thereby limit expansion of the portion of the infusion set caused by increased pressure within the infusion set.

68. The method of claim 66, wherein the optical detector receives less light from the optical emitter when the portion of the infusion set tubing expands due to increased pressure within the infusion set.

69. The method of claim 66, wherein the method further comprises selecting an infusion set wherein the portion of the infusion set disposed between the optical emitter and the optical detector has a wall thickness which is thinner that the wall thickness of adjacent sections of the infusion set.

70. The method of claim 62, wherein the at least one protrusion comprises at least one flange disposed on the tubing.

71. The method of claim 62, wherein the method further comprises disposing an optical bubble detector in the infusion set.

72. The method of claim 71, wherein the optical bubble detector comprises a sample cell and an optical emitter and an optical receiver.

73. The method of claim 72, wherein the optical receiver receives a first amount of light from the optical emitter when the sample cell is not disposed between the optical emitter and the optical detector, a second amount of light less than the first amount of light when the sample cell is disposed between the optical emitter and the optical detector and the sample cell is empty or a bubble is present in the sample cell, and a third amount of light less than the second amount of light when then sample cell is disposed between the optical emitter and the optical detector and the sample cell is filled with a liquid.

74. The method of claim 72, wherein the sample cell comprises a triangular cross-section.

75. The method of claim 74, wherein the sample cell further comprises a base portion disposed along an edge of the sample cell and extending outwardly from the sample cell, the base portion having parallel side walls such that a beam of light will pass through the base portion with minimal refraction.

76. A method for forming a feeding set, the method comprising:

selecting an infusion set having an inflow line and an outflow line; and connecting the inflow line to a first connector and the outflow line to a second connector, wherein at least one of the first connector and the second connector has a sample cell disposed therein for monitoring the presence of air bubbles passing through the infusion line, the sample cell comprising a rigid conduit having two non parallel side walls; and disposing the sample cell between an optical emitter and an optical detector such that the optical detector receives a first amount of light from the optical emitter when the sample cell is properly disposed between the optical emitter and optical detector, a second amount of light greater than the first amount of light when the sample cell is properly disposed between the emitter and detector and a either a bubble is present in the sample cell or the sample cell is empty, and a third amount of light greater than the second amount of light when the sample cell is not properly disposed between the optical emitter and optical detector.

77. The method of claim 76, wherein the method further comprises disposing an anti-freeflow occluder in the tubing at a fixed distance relative to one of the first and second connectors, the occluder comprising a solid head portion attached to a connector by a stem portion, the stem portion creating a conduit within the tubing for fluid flow, and the head portion contacting the inner wall of the tubing sufficiently to prevent flow past the head portion until sufficient pressure is generated to expand the tubing somewhat.

78. The method of claim 76, wherein the method further comprises a pressure sensing portion of the infusion set configured for placement between an optical emitter and an optical detector such that increases in pressure within the tubing increase the diameter of the tubing sufficient to reduce the amount of light transmitted to the optical detector from the optical emitter.

79. A method for forming a feeding set, the method comprising:

selecting an infusion set having a pump engaging portion, an inflow line and an outflow line; and connecting the inflow line and one end of the pump engaging portion to a first connector and the outflow line and the other end of the pump engaging portion to a second connector;

disposing an occluder inside the tubing of the infusion set;

disposing a bubble detector in the feeding set, the bubble detector configured for placement between an optical emitter and an optical receiver such that a portion of the light emitted by the emitter reaches the receiver when the bubble detector is placed between the emitter and receiver and filled with a fluid, and where a greater portion of the light emitted by the emitter reaches the receiver when a bubble is present in the bubble detector; and wherein a portion of the pump engaging portion is configured for placement between an optical emitter and an optical receiver such that increases in fluid pressure within the infusion set cause an increase in the diameter of the portion of the pump engaging portion sufficient to cause a reduction in the amount of light emitted by the emitter which reaches the receiver.

80. An infusion set tube, the tube being configured for insertion into a pump and for being connected to an inflow line and an outflow line by an inflow connector and an outflow connector, the infusion set rube comprising:

a length of resilient tubing; and a plurality of flanges formed integrally with the tubing, the flanges being spaced so as to form at least one monitoring portion and a pump portion wherein the flanges are configured for insertion into corresponding recesses in a pump housing or pump cartridge to thereby inhibit movement of the at least one monitoring portion, and wherein the pump portion is configured for being worked upon by a pump.

* * * * *